United States Patent
Vernhes et al.

(10) Patent No.: US 6,623,964 B2
(45) Date of Patent: Sep. 23, 2003

(54) METHOD FOR TREATMENT OF AN AQUEOUS FLUX BY ELECTROPULSATION OF A FIELD PARALLEL TO THE FLOW, PULSATION CHAMBER AND USES THEREOF

(75) Inventors: Marie-Christine Vernhes, Lavaur (FR); Pierre-André René Cabanes, Paris (FR); Justin Teissie, Ramonville St-Agne (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 09/975,931

(22) Filed: Oct. 15, 2001

(65) Prior Publication Data

US 2002/0155611 A1 Oct. 24, 2002

Related U.S. Application Data

(63) Continuation of application No. PCT/FR00/00983, filed on Apr. 14, 2000.

(30) Foreign Application Priority Data

Apr. 15, 1999 (FR) ............................................ 99 04751

(51) Int. Cl.[7] ............................................ C12N 15/02
(52) U.S. Cl. ........................ 435/450; 435/461; 435/470; 435/471; 435/173.6; 435/173.7; 435/285.2; 536/25.41; 424/94.1
(58) Field of Search ................................ 435/461, 450, 435/470, 471, 173.6, 173.7, 285.2; 536/25.41; 424/94.1

(56) References Cited

U.S. PATENT DOCUMENTS

| | | |
|---|---|---|
| 3,933,606 A | 1/1976 | Harms |
| 4,578,168 A | 3/1986 | Hofmann |
| 4,764,473 A | 8/1988 | Matschke et al. |
| 4,946,793 A | 8/1990 | Marshall, III |
| 4,970,154 A | 11/1990 | Chang |
| 5,612,207 A | 3/1997 | Nicolau et al. |

FOREIGN PATENT DOCUMENTS

| | | |
|---|---|---|
| BE | 466068 | 12/1946 |
| CH | 319956 | 3/1957 |
| DE | 38 27 414 A1 | 8/1989 |
| EP | 0 223 110 | 5/1987 |

OTHER PUBLICATIONS

J. Bernhardt et al., "On the Generation of Potential Differences across the Membranes of Ellipsoidal Cells in an Alternating Electrical Field," *Biophysik*, V. 10, 1973, pp. 89–98.

Kazuhiko Kinosita et al., "Voltage–Induced Conductance in Human Erythrocyte Membranes," *Biochimica et Biophysica Acta.*, V. 554, 1979 pp. 479–497.

Justin Teissie et al., "Electric Field Induced Transient Pores in Phospholipid Bilayer Vesicles," *Biochemistry*, V. 20, 1981 pp. 1948–1554.

S.Y. Ho et al., "Electroporation of Cell Membranes: A Review," *Critical Reviews in Biotechnology*, V. 16, 1996, pp. 349–362.

Lluis M. Mir et al., "Introduction of Definite Amounts of Nonpermeant Molecules into Living Cells after Electropermeabilization: Direct Access to the Cytosol," *Experimental Cell Research*, V. 175, 1988, pp. 15–25.

Tian Y. Tsong, "Electroporation of Cell Membranes," *Biophy. J.*, V. 60, 1991, pp. 297–306.

Ivan Hapala, "Breaking the Barrier: Method for Reversible Permeabilization of Cellular Membranes," *Critical Reviews in Biotechnology*, V. 17, 1997, pp. 105–122.

W.A. Hamilton et al., "Effects of High Electric Fields on Microorganisms: II. Mechanism of Action of the Lethal Effect," *Biochimica et Biophysica Acta*, V. 148, 1967, pp. 789–800.

A.J.H. Sale et al., "Effects of High Electric Fields on Microorganisms: I: Killing of Bacteria and Yeasts," *Biochim. Biopohys. Acta*, V. 148, 1967, pp. 781–788.

A.J.H. Sale et al., "Effects of High Electric Fields on Microorganisms: III: Lysis of Erythrocytes and Protoplasts," *Biochim. Biophys. Acta*, V. 163, 1968, pp. 37–43.

H. Hülsheger et al., "Killing of Bacteria with Electric Pulses of High Field Strength," *Radiat. Environ. Biophys.*, V. 20, 1981, pp. 53–65.

H. Hülsheger et al., "Electric Field Effects on Bacteria and Yeast Cells," *Radiat. Environ. Biophys.*, V. 22, 1983, pp. 149–162.

Akira Mizuno et al., "Destruction of Living Cells by Pulsed High–Voltage Application," *IEEE Transactions on Industry Applications*, V. 24, 1988, pp. 387–394.

M.M. Kekez et al., "Contribution to the Biophysics of the Lethal Effects of Electric Field on Microorganisms," *Biochim. Biophys. Acta*, V. 1278, 1996, pp. 79–88.

T. Grahl et al., "Killing of Microorganisms by Pulsed Electric Fields," *Appl. Microbiol. Biotechnol.*, V. 45, 1996, pp. 148–157.

(List continued on next page.)

*Primary Examiner*—James Ketter
(74) *Attorney, Agent, or Firm*—Young & Thompson

(57) ABSTRACT

The invention concerns a method for treating an aqueous flow colonized by cells with a pulsed electric field applied to a flow, characterized in that the applied field is substantially parallel to the direction of flow and to its application to the transfer of nucleic acids (RNA, DNA, oligonucleotides) into cells, to the transfer of proteins to cells, to the extraction of cytoplasmic macromolecules and molecules contained in the cells, to cell fusion and the production of hybrids and/or to insertion of membrane proteins. It also concerns an electropulsing chamber, a method for destroying cells and a membrane permeabilization method.

30 Claims, 3 Drawing Sheets

OTHER PUBLICATIONS

Sheshakamal Jayaram et al., "Kinetics of Sterilization of *Lactobacillus brevis* Cells by the Application of High Voltage Pulses," *Biotechnology and Bioengineering,* V. 40, 1992, pp. 1412–1420.

Dietrich Knorr et al., "Food Application of High Electric Field Pulses," *Trends in Food Science and Technology,* V. 51, 1994, pp. 71–75.

Bai–Lin Qin et al., "Nonthermal Pasteurization of Liquid Foods Using High–Intensity Pulsed Electric Fields," *Critical Reviews in Food Science and Nutrition,* V. 36, 1996, pp. 603–627.

Bai–Lin Qin et al., "Inactivating Microorganisms Using a Pulsed Electric Field Continuous Treatment System," *IEEE Transactions on Industry Application,* V. 34, 1998, pp. 43–50.

J. Teissié et al., "Electrofusion of Large Volumes of Cells in Culture," *Bioelectrochemistry and Bioenergetics,* V. 19, 1988, pp. 49–57.

J. Teissié et al., "Electrofusion of Large Volumes of Cells in Culture: Part II: Cells Growing in Suspension," *Bioelectrochemistry and Bioenergetics,* V. 19, 1988, pp. 59–66.

S. Sixou et al., "Specific Electropermeabilization of Leucocytes in a Blood Sample and Application to Large Volumes of Cells," *Biochimica et Biophysica Acta,* V. 1028, 1990, pp. 154–160.

J. Teissié et al., "Large Volume Cell Electropermeabilization and Electrofusion by a Flow Process," Allen Ed, Birkhauser Press, 1992, pp. 449–466.

Marie–Pierre Rols et al., "Highly Efficient Transfection of Mammalian Cells by Electric Field Pulses," *Eur. J. Biochem.,* V. 206, 1992, pp. 115–121.

U. Brüggemann et al., "Low–Oxygen–Affinity Red Cells Produced in a Large–Volume, Continuous–Flow Electroporation System," *Transfusion,* V. 35, 1995, pp. 478–486.

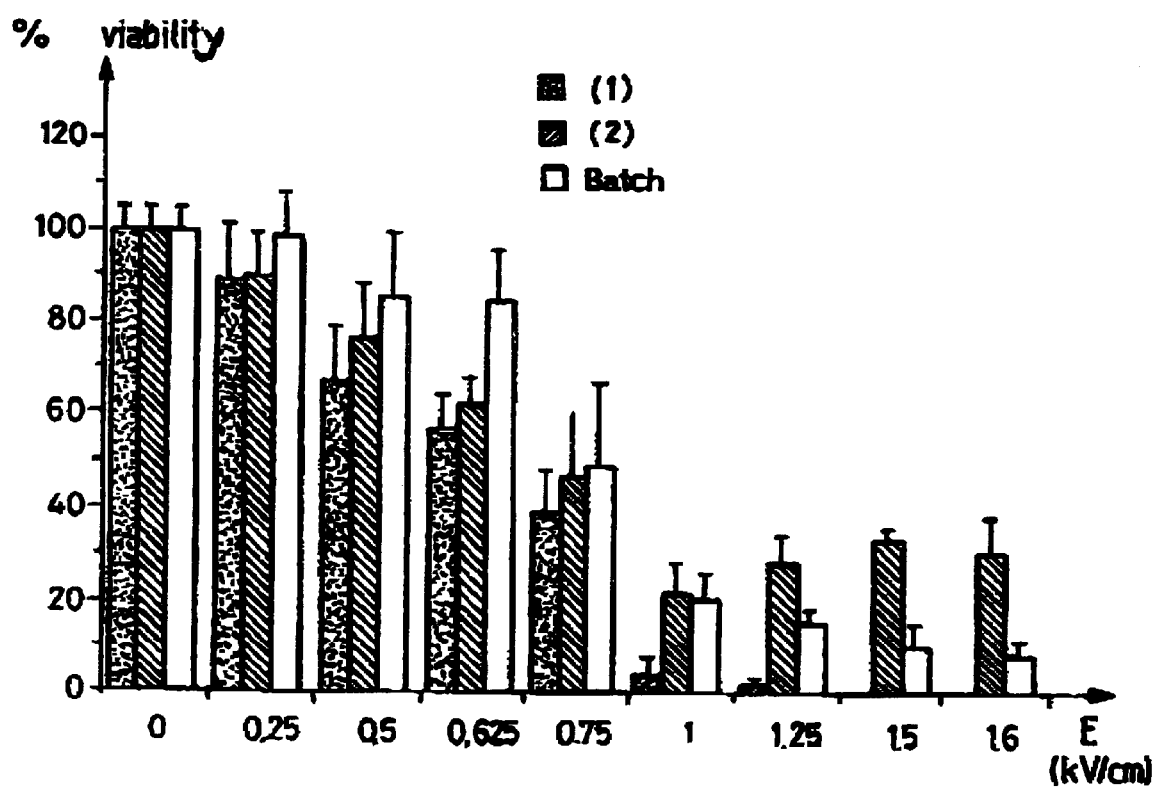
FIG_1

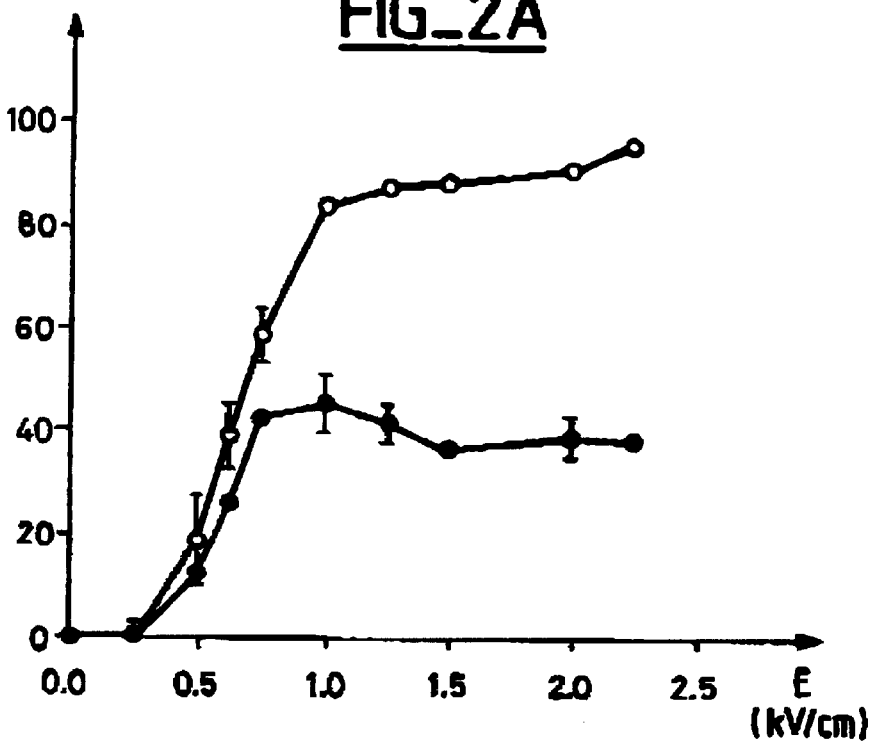
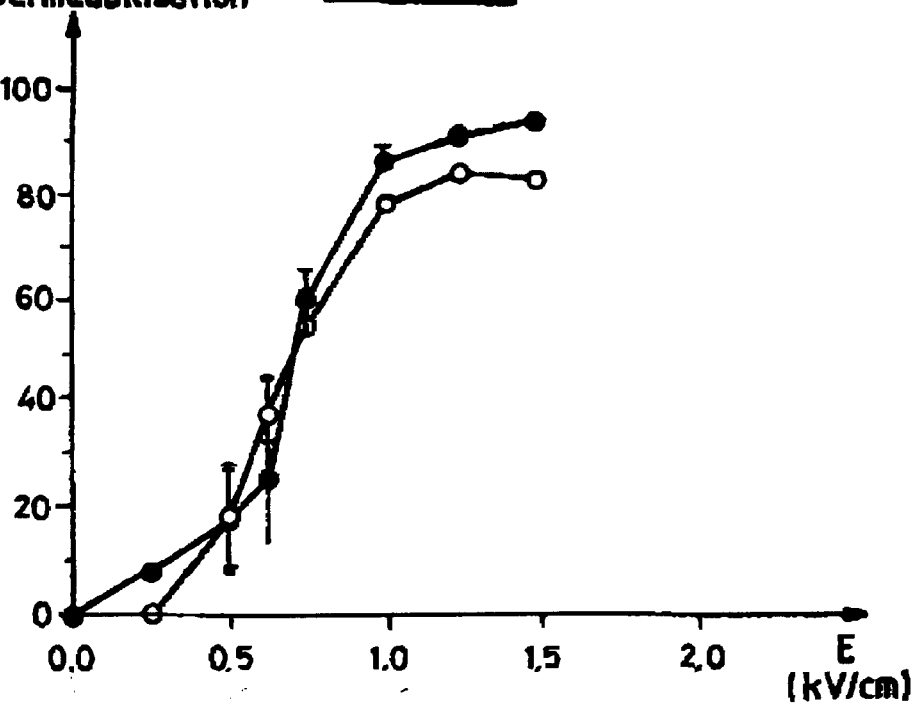

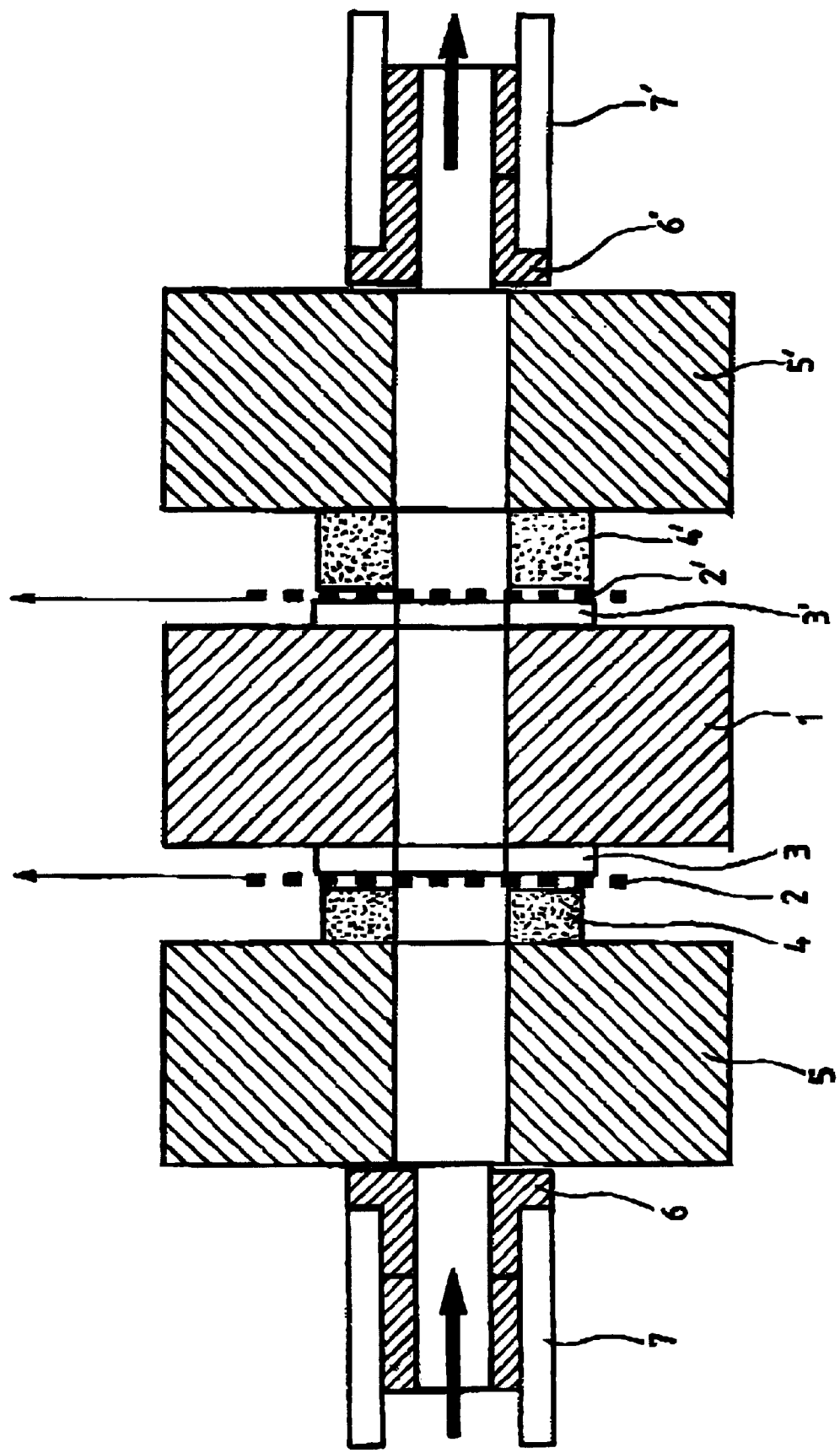
FIG_3

METHOD FOR TREATMENT OF AN AQUEOUS FLUX BY ELECTROPULSATION OF A FIELD PARALLEL TO THE FLOW, PULSATION CHAMBER AND USES THEREOF

This is a continuation of co-pending international application No. PCT/FR00/00983, filed on Apr. 14, 2000, which designated the United States of America.

The present invention relates to a method for treating an aqueous flow colonised by cells by applying an electric field parallel to the flow direction, to a flow and electropulsing chamber and to its application to cell treatment, in particular cell destruction, transmembrane transfer of molecules, membrane fusion and insertion of membrane proteins.

The application of an electric field to cells is known: when a cell is placed in an electric field, it distorts the field lines, causing an accumulation of charge on the cell surface. This results in an induced transmembrane potential difference $\Delta V$ which is superimposed on the native difference $\Delta \Psi_0$ [Bernhardt J. and Pauly H. (1973): (1)].

The most complete formula used in the case of a field with square wave kinetics and a spherical cell in suspension is as follows [Kinosita and Tsong (1979) (2)]:

$$\Delta V(t) = f g(\lambda) r E(t) \cos \theta (1 - e^{-t/\tau_p}) \quad \text{eq 1}$$

The expression for this potential difference induced at a point M at time t is a fraction of:

E: the intensity of the applied electric field;

f: the form factor for the cell (1.5 in the case of a sphere);

$g(\lambda)$: factor (of the membrane permeability $\lambda$) linked to the conductivities of the external and internal media and to that of the membrane;

r: the cell radius;

$\theta$: the angle between the macroscopic electric field vector and the normal to the plane of the membrane at the point considered, M;

$\tau_p$: the charge time for the membrane capacity (of the order of one microsecond);

t: time of application of field.

When the pulse duration is much longer than the time to charge the membrane ($t \gg \tau_p$), the term ($1 - e^{-t/\tau_p}$) tends towards 1 to give the stationary state of the conventional formula:

$$\Delta V(t) = f g(\lambda) r E(t) \cos \theta \quad \text{eq 2}$$

The term in $\cos \theta$ indicates that for a given field, the amplitude of this potential difference is not identical at every point of the cell. It is a maximum at points facing the electrodes (poles) and reduces along the cell surface to become zero at the equator.

This potential difference generated by the field is added to the standing potential difference $\Delta \Psi_0$. This produces a resultant potential difference $\Delta V_r$.

$$\Delta Vr = \Delta \Psi_0 + \Delta V \quad \text{eq 3}$$

For the cellular hemisphere facing the anode, the numerical values of $\Delta \Psi_0$ and $\Delta V$ add to take into account the vector of the field effect, causing membrane hyperpolarisation. In contrast, for the hemisphere facing the cathode, the numerical values of $\Delta \Psi_0$ and $\Delta V$ subtract and the membrane undergoes depolarisation.

When this resulting membrane potential difference exceeds a threshold value estimated to be 200–250 mV [Teissié and Tsong (1981): (3)], a permeabilisation phenomenon is induced [Ho and Mittal (1996): (4)].

The membrane structure responsible for this membrane permeability is unknown at the present time, and the term "transient permeabilisation structure" (TSP) is preferentially used, which is usually expressed by the term "pores".

If the electropermeablisation conditions are controlled, this permeabilisation phenomenon is transient and reversible, and has little or no effect on cellular viability. This property induced by the field can provide direct access to the cytoplasmic contents [Mir et al., (1988): (5); Tsong (1991): (6); Hapala, (1997): (7)]. This allows foreign molecules that are naturally non permeating to penetrate and thus modifies the contents either transiently or permanently (electrocharging, electrotransformation, electroinsertion).

In contrast, under particularly drastic electropulsing conditions, electropertneabilisation is an irreversible phenomenon that leads to cell death, or electromortality [Sale and Hamilton (1967): (8); Sale and Hamilton (1967): (9), (1968): (10), Hulsheger et al., (1981): (11), (1983): (12); Mizuno and Hori (1988): (13); Kekez et al., (1996): (14), Grahl and Märkl (1996): (15)]. This property has been used either to lyse cells to recover a metabolite of interest, not naturally excreted by the cell, or to eradicate cells from the environment (disinfecting) or from alimentary fluids (non thermal sterilisation) [Jayaram et al., (1992): (16), Knorr et al., (1994): (17); Qin et al., (1996): (18); Qin et al., (1998): (19)].

The prior art discloses two systems for applying a pulsed electric field to a liquid medium, and the choice depends primarily on the volume of liquid to be treated. Fixed bed, or batch, pulse systems have been described. Such units (chambers) and methods can only treat small volumes, however, of the order of a fraction of a milliliter. The technical limit is linked to the power available from the electric pulse generators at a reasonable cost. In addition to research work, such an approach can produce genetically modified organisms (GMO) on an industrial scale.

Further, the application of a pulsed electric field to a flow has been described, which allows a flowing cell suspension to be treated. For the flow method, two strategies have been described: continuous flow and sequential flow.

In the second model, sequential flow, the pulse chamber is filled, the flow is stopped, the field is applied, the chamber is then emptied then refilled. The cells are immobile during application of the field. Thus, there are no hydrodynamic stresses. The operating conditions are thus identical to those described for fixed bed experiments. The flow rate is limited by the need to stop the flow to apply the pulses. However, large volumes can be used, for long periods.

The advantage of a flow system is that large volumes can be treated. The flow consists of an uninterrupted flow through the chamber and synchronising a series of pulses with the flow. Thus, it is possible to apply a defined number of pulses to the cells during their residence time in the pulse chamber. The cells are then moving and subjected to hydrodynamic stresses of deformation and orientation. The flow rate can be very high, being only limited by the frequency of the pulses. This approach, therefore, means that large volumes can be treated quickly.

To carry out certain sequential and/or continuous treatments of flows and in particular to treat certain colonised flows, it is known to use flow systems that apply a field perpendicular to the direction of flow [Teissié and Conte (1988): (20); Teissié and Rols (1988): (21); Sixou and Teissié (1990): (22), Teissié et al., (1992): (23), Rols et al., (1992): (24); Bruggeman et al., (1995): (25); Qin et al., (1996): (18)].

Systems in which the flow and the electrodes are coaxial have also been proposed, also systems in which a non uniform field is applied that is always perpendicular to the flow [Qin et al., (1996): (18); Qin et al., (1998): (19)]. In all of the prior descriptions, the applied field is perpendicular to the direction of flow.

According to Bruggeman et al., (1995): (25), for a given value of the electric field, the flow technique results in lower efficiency than that obtained with a batch system, as demonstrated when electrocharging inositol hexaphosphate onto red corpuscles. According to that method, an increase in the electric field intensity by 10% is necessary to obtain similar results to those obtained with a batch system in a continuous flow system. A more intense field intensity has to be used, and thus the costs are higher. In terms of charging efficacy, the flow approach enables a much larger volume to be treated.

It has now been shown that applying an electric field in a manner that is substantially parallel to the flow can result in higher efficiency for continuous flow treatment methods.

With certain species, in the case of electromortality, the method of the invention can completely eradicate the population, while this is not possible using known methods and units with a perpendicular field method or a fixed bed method.

Further, complete permeabilisation of the population of deformable spherical cells is possible, while a partial effect is obtained with known methods and units.

Further, in accordance with the invention, it is possible to operate with lower fields, and thus operating costs are improved compared with the batch (fixed bed) technique.

Finally, this configuration can also be advantageous for non spherical cell systems, for example rod cell systems, which experience enforced orientation due to flow stresses.

In a first aspect, the invention provides a method for treating an aqueous flow colonised by cells using a pulsed electric field applied to the flow, characterized in that the electric field is applied substantially parallel to the direction of flow.

In a further aspect, the invention provides a flow and pulse chamber. Devices for treating aqueous flows using a field are known. In accordance with the invention, the chamber comprises at least two electrodes that can create a uniform field substantially parallel to the direction of the flow between them.

One manner of producing such a field configuration consists of providing electrodes that can produce a uniform field parallel to the direction of the flow between them, for example electrodes through which the flow passes. Such electrodes can be perforated plates, screens, cloth or bars, for example.

The transverse cross section of the pulse chamber can be circular or polygonal, or it may be elliptical in shape. When the electrodes are of the screen or bar type, the electrodes are parallel. However, other configurations that can produce a uniform field parallel to the flow can be envisaged.

The longitudinal cross section does not necessarily have parallel edges. The colonised flow can be subjected to a hydrodynamic stress before, after or during its passage through the chamber. More complex geometries can be envisaged, in particular venturi tubes, where a hydrodynamic stress will be applied during passage through the chamber. Such stresses can be applied in a known manner by selecting the configuration of the flow inlet and outlet channels into and out of the chamber, and the flow towards the chamber, and the configuration of the chamber itself.

Applications of the method and chambers of the invention that can be cited include cell destruction of undesirable cells present in a colonised aqueous medium and the extraction of cytoplasmic metabolites by membrane permeabilisation, also modification of the cytoplasmic contents by transfer of small molecules or macromolecules (peptides, proteins, nucleic acids: oligonucleotides, RNA, DNA), cell fusion and insertion of transmembrane proteins.

Further, the invention concerns a method for destroying cells in which a colonised aqueous flow is subjected to an electric field substantially parallel to its direction of flow. It also concerns a method for membrane permeabilisation of cells in a colonised aqueous flow, by applying an electric field substantially parallel to the flow.

Finally, the present invention concerns the application of the method to the transfer of nucleic acids (RNA, DNA, oligonucleotides) into cells, to the transfer of proteins into cells, to the extraction of cytoplasmic macromolecules and molecules contained in the cells, to cell fusion and to the production of hybrids and/or insertion of membrane proteins.

The term "colonised flow" as used in the invention means any domestic, natural or industrial aqueous medium containing undesirable cells. These cells or microorganisms can in general be any monocellular organism developing or living in aqueous flows. In some cases, they have to be eradicated for sanitary or public health reasons, for ecological reasons or to maintain industrial equipment. Certain cells proliferate in certain media and their presence or multiplication in the water and liquid to be treated is deleterious to the operation of facilities, or to health or well-being. The colonised flow can be an aqueous medium containing cells or micro-organisms producing molecules of interest the contents of which are to be recovered, or into which molecules or macromolecules that affect their activity can be introduced (genetic modification, for example).

They may be deformable spherical cells, but in general they can be any cell system that is sensitive to an electric field with a view to electromortality or the other applications of the methods of the invention. In particular, cell systems with other configurations, such as rods, bacteria or yeasts, can be treated.

The present invention will be better understood from the following detailed description, made with reference to the accompanying drawings in which:

FIG. 1 pertains to amoebas, and shows the results, in terms of percentages cell viability, of applying a pulsed electric field where the field is applied respectively parallel to a flow (1-black), perpendicular to a flow (2-grey) and discontinuously (batch-white).

FIGS. 2A and 2B show the percentage permeabilisation of the cell membrane of amoebas, the efficacy of a field applied with intensity E (kV/cm) perpendicular to the direction of flow (flow-•-2A) and that of a field applied parallel to the direction of flow (flow-•-2B) compared with that of a field applied discontinuously (batch: -o-, 2A and 2B)

FIG. 3 shows a diagrammatic view of a cell for use in the invention.

In accordance with the invention, and preferably, the flow is continuous. However, the method of the invention can also be carried out with a sequential flow.

Values defining the applied electric field depend on the unit and on the intended application of the method. The difference in electric potential applied between the two electrodes is a function of the envisaged use. It is often under the control of the distance between the two electrodes. It must enable ranges of electric field in the range from a few V/cm to tens of kV/cm to be encompassed. The intensity of the applied electric field can be between 0.1 and 100 kV/cm.

The pulse profile is optimised to the type of application. It can be a square wave, trapezoidal wave, sinusoidal wave, triangular wave or an exponential decay wave. The pulses can be unipolar or bipolar.

The pulse frequency is optimised for the type of application, but is preferably below a MHz.

The pulsing system developed in the laboratory to carry out the method of the invention comprises the following elements: a cell reservoir provided with a stirrer, a peristaltic pump, a pulse chamber and a discharge for treated flow that can recover the cells, and means for conveying the flow from the reservoir to the chamber and from the chamber to the discharge. An example of a chamber will be described below in detail.

The peristaltic pump (pump, Minipuls 3, Gilson) provides the cell reservoir with an overpressure, to drive the cell suspension towards the electropulsing chamber without passing between the rollers of the pump. This is provided with a flow measuring system to allow the flow to be accurately adjusted.

The flow Q used is based on the concept of residence time such that each cell entering the pulse chamber is subjected to the same electrical conditions. It is defined by the frequency (F), number (N) of pulses and the volume (V) of the pulse chamber by the following relationship:

$$Q(\text{ml/minute}) = \frac{\text{frequency (Hz)} \times 60 \times \text{volume of chamber (ml)}}{\text{Number of pulses applied}}$$

In accordance with the invention, the flow rate can be optimised for the type of application. The flow rate is of the order of 0.5 ml/min to several $m^3/s$.

The electrodes in the two systems are connected to a high voltage pulse generator (1.5 kV/cm, 8 amp, pulse duration (width) programmable from 5 $\mu s$ to 24 ms, frequency from 0.1 to 10 and up to 2000 Hs when driven externally) connected to an oscilloscope (Enertec) to enable the delivered electrical parameters to be viewed. The kinetic profile of the pulses delivered by the generator is a square wave, the field intensity remaining constant throughout the pulse period (T). The electropulser is flexible enough to allow the tension, duration, number and frequency of the pulses to be modulated.

EXAMPLE

Measurement Method

Experiments were carried out on amoebas in the vegetative form (*Naegleria lovaniensis* Ar9M1). The cell size was 18.2 $\mu m$ (8.5 $\mu m$–31.5 $\mu m$)×10.9 $\mu m$ (4 $\mu m$–21 $\mu m$). They were cultivated under axenic conditions in plastic trays at 37° C. using Chang culture medium. The pulsing medium was filtered river water with a conductance of the order of 200 $\mu S/cm$.

The viability was evaluated 24 hours after electric treatment by means of the crystal violet dye technique.

Cell permeabilisation was quantified by flow cytometry using a naturally non permeating fluorescent marker, propidium iodide.

1) Description of Fixed Bed Pulsing System

The pulsing chamber was constituted by two flat stainless steel plate electrodes kept parallel by insulating blocks. The inter-electrode distance was 0.4 cm.

2) Description of Flow Electrodes for a Field Perpendicular to the Direction of Flow (Comparative).

The stainless steel electrodes were constituted by two parallel plates separated by an inter-electrode distance of 0.4 cm. The volume of the parallelepipedal pulse chamber was 0.2 ml.

3) Description of Flow Electrodes for a Parallel Field.

The steel electrodes used were screens constituted by a mesh (80 $\mu m$×100 $\mu m$) through which the cells passed. The inter-electrode distance was 0.93 cm and the volume of the pulse chamber was 0.117 ml.

In the two cases, the colonised aqueous medium was pumped from a stirred reservoir.

The aqueous flow created was then driven into a conduit. The pulse chamber delimited by the two electrodes regardless of the field orientation was constituted by a portion of the conduit delimited by two electrodes. The electrodes were in the form of a screen allowing the flow to pass through in the case of a parallel field. The electrodes were connected to an electropulser. The two flow pulse chambers had different volumes, which explains why the flow rates used to produce the same electropulsing conditions were different. The flow rate in the case where the field was perpendicular to the direction of flow was 1.2 ml/min and that of the field configured parallel to the direction of flow was 0.71 ml/min.

The liquid supplied via a channel connected to a supply pump passed through the first electrode, traversed the chamber, then through the second electrode before being recovered.

1-The Body

A cylindrical hole (diameter of the order of a few millimeters) was perforated in a sheet of Plexiglass (1 to 10 mm thick).

Material: Plexiglass, an electrical insulator, although any other insulating material can be envisaged, in particular if suitable for moulding.

The transverse cross sectional shape was selected for ease of manufacture (one shot).

The longitudinal cross section had parallel edges, ensuring good field homogeneity and thus good cell treatment homogeneity.

2-The Electrodes:

Steel cloth (screen) or stainless steel needles (bars) were used. For the cloth, the weave was selected to have a fine mesh to ensure good field conformity. This allowed the cells to be treated more homogeneously.

Any electrically conducting material can be used to constitute the electrodes.

The electrodes were connected to an electric pulse generator.

The electrodes were placed against the body of the chamber.

A seal was obtained by means of O-rings and silicone.

3-Fluid Supply Connectors:

These were inserted into Plexiglass plates kept in intimate contact with the electrodes. O-rings and silicone provided a seal.

FIG. 3 shows the flow supply line connected via a connection 6 to a connector block 5. Electrode 2 was held between an outer O-ring 4 and an inner O-ring 3. The inner O-ring 3 provided a seal with body 1.

A further inner O-ring 3' ensured a seal with body 1 and held the second electrode 2'. Along the path of the flow, elements 4', 5', 6', 7', analogous to elements 4, 5, 6, 7 above, directed the flow towards the outlet.

Electrodes 2, 2' were connected to the electric pulse generator (not shown).

Results

For the three electropulse techniques (batch, field parallel to flow, field perpendicular to flow), the efficiency for destroying amoebas was measured. The cells were electropulsed, in all cases, by ten pulses of 10 ms delivered with a frequency of 1 Hz. The results concerning the change in viability with the electric field intensity are shown in FIG. 1.

With the configuration with the field parallel to the direction of flow, a viability drop profile was obtained in which the viability was more affected as the electric field intensity increased.

The use of a field parallel to the direction of flow produced the lowest viabilities for each intensity of electric field studied, and thus proved itself to be a highly effective technique for eradicating amoebas. When the field value was 1.5 kV/cm, the amoebas were completely eliminated.

Further, the results obtained with a field perpendicular to the direction of flow showed that in that type of configuration, for high field values (1 kV/cm), an increase in electric field intensity did not result in an increase in mortality. 25% of the population was unaffected by the lytic effect of the field.

FIGS. 2A and 2B compare the profiles obtained for permeabilisation as a function of the electric field intensity for the two flow techniques with respect to the permeabilisation profile obtained for the batch system. In the three cases, the cells were electropulsed by ten pulses of 10 ms delivered with a frequency of 1 Hz.

In the configuration in which the field was perpendicular to the flow (2A), over an electric field intensity range of 0 to 0.75 kV/cm, an increase in the electric field intensity resulted in an increase in permeabilisation. The increase in the field intensity did not cause an increase in the number of permeabilised cells. A plateau was produced at only 40%.

In the case where the field was parallel to the flow (2B), over all of the field values used, the increase in the electric field intensity was correlated to an increase in the degree of permeabilisation. As regards the efficiency of flow permeabilisation, the use of a field parallel to the direction of flow produced the best results. An increase in the field intensity allowed more than 90% of the population to be permeabilised.

Further, permeabilisation of the flow, with a field parallel to the flow, was triggered for values below the critical value for the batch system (0.25 kV/cm).

REFERENCES

1. Bernhardt J. et al., Biophysik 10:89–98 (1973)
2. Kinosita K. et al., Biochim. Biophys. Acta 554:479–497 (1979)
3. Teissié J. et al., Biochemistry 20: 1548–1554 (1981)
4. Ho S. Y. et al., Critical Reviews in Biotechnology, 16: 349–362 (1996)
5. Mir L. M. et al., Experimental Cell Research 175: 15–25(1988)
6. Tsong T. Y., Biophys. J. 60: 297–306 (1991)
7. Hapala I, Critical Reviews In Biotechnology 17: 105–122 (1997)
8. Hamilton W. A. et al., Biochim. Biophys. Acta. 148: 789–800 (1967)
9. Sale J. H. et al., Biochim. Biophys. Acta. 148: 781–788 (1967)
10. Sale J. H. et al., Biochim. Biophys. Acta. 163: 37–43 (1968)
11. Hulsheger H. et al., Radiat. Environ Biophys. 20: 53–65 (1981)
12. Hulsheger H. et al., Radiat. Environ. Biophys. 22:149–162(1983)
13. Mizuno A. et al., IEEE Transactions on Industry Applications 24: 387–394 (1988)
14. Kekez M. M. et al., Biochim. Biophys. Acta 1278: 79–88 (1996)
15. Gralht T. et al. Appl. Microbiol. Biotechnol. 45: 148–157 (1996)
16. Jayaram S. et al., Biotechnology and Bioengineering. 40: 1412–1420 (1992)
17. Knorr D. et al, Trends in Food Science and Technology 51: 71–75 (1994)
18. Qin B-L. et al., Critical Reviews in Food Science and Nutrition. 36: 603–627(1996)
19. Qin B-L. et al., IEEE Transactions on Industry Application. 34: 43–50 (1998)
20. Teissié J. et al., Bioelectrochem. Bioenerg. 19: 49–57 (1988)
21. Teissié J. et al., Bioelectrochem. Bioenerg. 19: 59–66 (1988)
22. Sixou S. et al., Biochim. Biophys. Acta. 1028: 154–160 (1990)
23. Teissié J. et al., "Charge and Field effects in Biosystems III", Allen Ed, Birkhauser press pp 449–466 (1992)
24. Rols M. P. et al., Eur. J Biochem. 206: 115–121(1992)
25. Bruggemann U. et al., Transfusion 35: 478–486 (1995)

What is claimed is:

1. A method for membrane permeabilisation of cells, in which an aqueous flow is colonized by cells, comprising subjecting the flow to a pulsed electric field applied to the flow in a manner substantially parallel to the direction of the flow, wherein the applied electric field is of 0.1 to 100 kV/cm.

2. The method according to claim 1, wherein the flow is sequential.

3. The method according to claim 1, wherein the flow is continuous.

4. A method for fusing cells and producing hybrids comprising:
   (1) colonizing an aqueous flow by the cells;
   (2) subjecting the flow to a pulsed electric field applied to the flow in a manner substantially parallel to the direction of the flow, whereby cells are fused and hybrids produced.

5. The method according to claim 1, wherein applied pulsed electric field has pulses with a square wave profile, a triangular wave profile, a sinusoidal wave profile or a trapezoidal wave profile.

6. The method according to claim 1, wherein the applied pulsed electric field has pulses delivered at a frequency of less than one MHz.

7. The method according to claim 1, wherein the flow is subjected to a hydrodynamic stress.

8. A method for inserting membrane proteins in cells comprising:
   (1) colonizing an aqueous flow by the cells;
   (2) subjecting the flow to a pulsed electric field applied to the flow in a manner substantially parallel to the direction of the flow, whereby membrane proteins are inserted in cells.

9. A method for transferring nucleic acids or proteins into cells, comprising:
   (1) colonizing an aqueous flow by the cells;
   (2) subjecting the flow to a pulsed electric field applied to the flow in a manner substantially parallel to the direction of the flow, whereby nucleic acids or proteins are transferred into cells.

10. A method for extracting cytoplasmic macromolecules or molecules contained in cells comprising:
    (1) colonizing an aqueous flow by the cells;
    (2) subjecting the flow to a pulsed electric field applied to the flow in a manner substantially parallel to the direction of the flow, whereby cytoplasmic macromolecules or molecules contained in cells are extracted.

11. The method according to claim 8, wherein the applied pulsed electric field has pulses delivered at a frequency of less than one MHZ.

12. The method according to claim 8, wherein the flow is subjected to a hydrodynamic stress.

13. The method according to claim 9, wherein the flow is sequential.

14. The method according to claim 9, wherein the flow is continuous.

15. The method according to claim 9, wherein applied pulsed electric field has pulses with a square wave profile, a sinusoidal wave profile or a trapezoidal wave profile.

16. The method according to claim 9, wherein the applied pulsed electric field has pulses delivered at a frequency of less than one MHz.

17. The method according to claim 9, wherein the flow is subjected to a hydrodynamic stress.

18. The method according to claim 10, wherein the flow is sequential.

19. The method according to claim 10, wherein the flow is continuous.

20. The method according to claim 10, wherein applied pulsed electric field has pulses with a square wave profile, a sinusoidal wave profile or a trapezoidal wave profile.

21. The method according to claim 10, wherein the applied pulsed electric field has pulses delivered at a frequency of less than one MHz.

22. The method according to claim 10, wherein the flow is subjected to a hydrodynamic stress.

23. The method according to claim 4, wherein the flow is sequential.

24. The method according to claim 4, wherein the flow is continuous.

25. The method according to claim 4, wherein applied pulsed electric field has pulses with a square wave profile, a sinusoidal wave profile or a trapezoidal wave profile.

26. The method according to claim 4, wherein the applied pulsed electric field has pulses delivered at a frequency of less than one MHz.

27. The method according to claim 4, wherein the flow is subjected to a hydrodynamic stress.

28. The method according to claim 8, wherein the flow is sequential.

29. The method according to claim 8, wherein the flow is continuous.

30. The method according to claim 8, wherein applied pulsed electric field has pulses with a square wave profile, a sinusoidal wave profile or a trapezoidal wave profile.

* * * * *